United States Patent [19]

Juner et al.

[11] 4,379,481
[45] Apr. 12, 1983

[54] X-RAY APPARATUS AND CLOSURE MECHANISM THEREFOR

[75] Inventors: Adolph Juner, City Island; David J. Haas, Suffern, both of N.Y.; Chester D. Rudd, Westwood, N.J.

[73] Assignee: North American Philips Corporation, New York, N.Y.

[21] Appl. No.: 205,553

[22] Filed: Nov. 10, 1980

Related U.S. Application Data

[63] Continuation of Ser. No. 864,504, Dec. 27, 1977, abandoned.

[51] Int. Cl.³ .................. G01N 23/00; G21F 7/00; A47G 5/02
[52] U.S. Cl. .................................. 160/310; 74/435; 192/135; 250/358.1
[58] Field of Search .................. 160/310, 331, 191; 250/358 R, 358 P, 358 T, 359, 358.1, 359.1; 192/135; 74/435

[56] References Cited

U.S. PATENT DOCUMENTS

| 816,496 | 3/1906 | McKenzie | 160/191 |
|---|---|---|---|
| 1,798,577 | 3/1931 | Ames | 160/310 X |
| 1,853,704 | 4/1932 | Standow | 160/310 |
| 1,897,391 | 2/1933 | Kelly | 160/191 X |
| 1,983,583 | 12/1934 | Timko | 160/331 X |
| 2,259,979 | 10/1941 | Norberg | 160/191 X |
| 2,466,103 | 4/1949 | Hiester | 160/310 X |
| 2,701,012 | 2/1955 | Loucony | 160/176 |
| 3,678,278 | 7/1972 | Peil | 250/358 R |
| 3,822,438 | 7/1974 | Takenaka | 74/435 X |
| 3,866,486 | 2/1975 | Lechner | 74/435 X |
| 3,915,273 | 10/1975 | Loschengruber | 192/135 |
| 4,003,267 | 1/1977 | Busch | 74/435 X |
| 4,020,346 | 4/1977 | Dennis | 250/358 R |
| 4,210,811 | 7/1980 | Dennhoven et al. | 250/358 R |

FOREIGN PATENT DOCUMENTS 25297 of 1902 United Kingdom .................. 74/435

*Primary Examiner*—Rodney H. Bonck
*Attorney, Agent, or Firm*—Paul R. Miller

[57] ABSTRACT

An apparatus for inspecting various articles in connection with the present invention comprises a structure for operating a retractable door which includes a shaft member, a flexible door member carried by and windable on the shaft member, a motor structure for driving the shaft member, and a gear train mechanically linking the motor and shaft member. The gear train includes a drive gear and a driven gear with the driven gear being connected to the shaft member and the drive gear being connected to and driven by the motor. The drive gear and driven gear both comprise gear teeth about only a portion of the respective circumferences. A switch member for controlling the motor is provided, and an actuating control structure is provided with respect to the drive gear for controlling the switch member.

14 Claims, 7 Drawing Figures

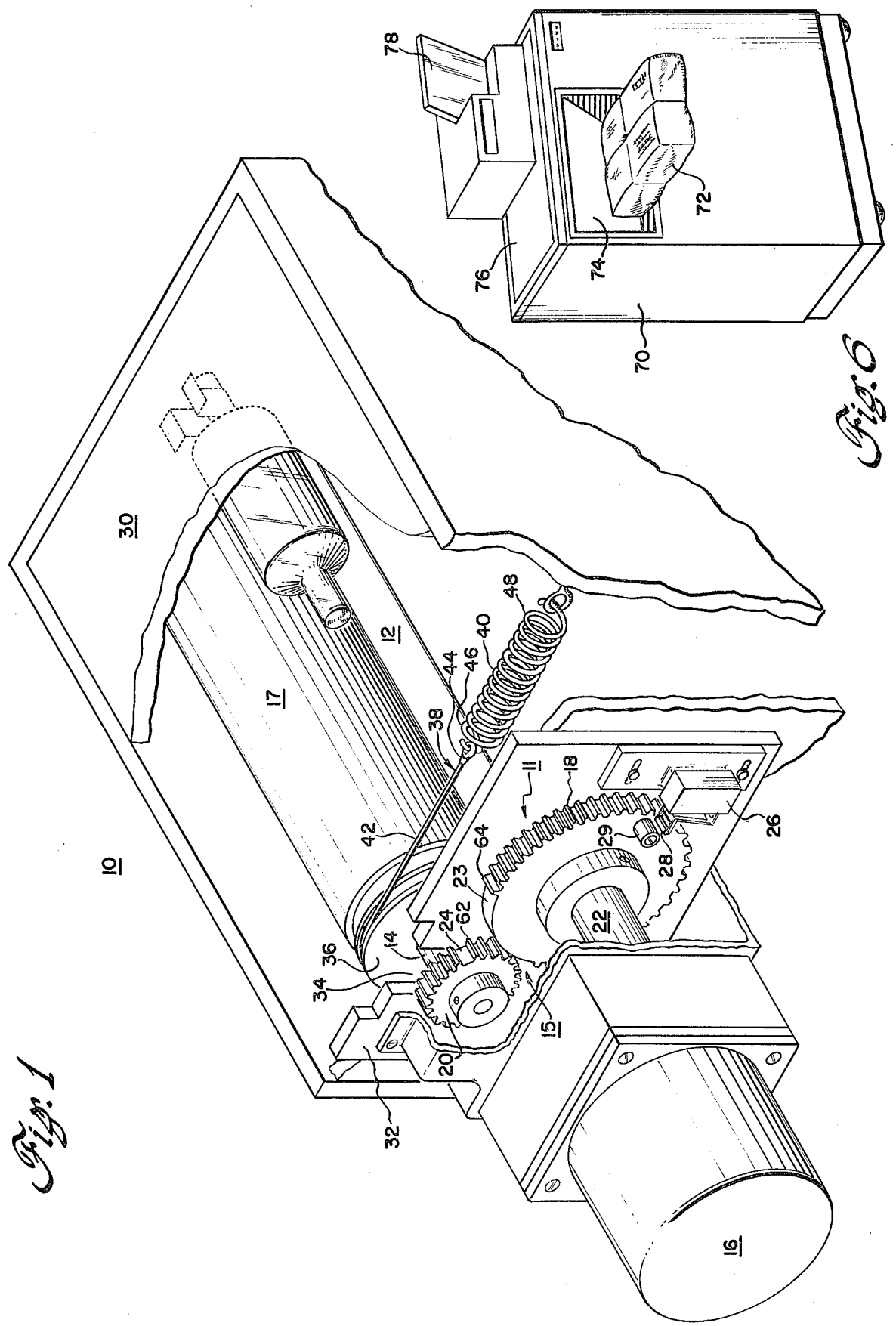

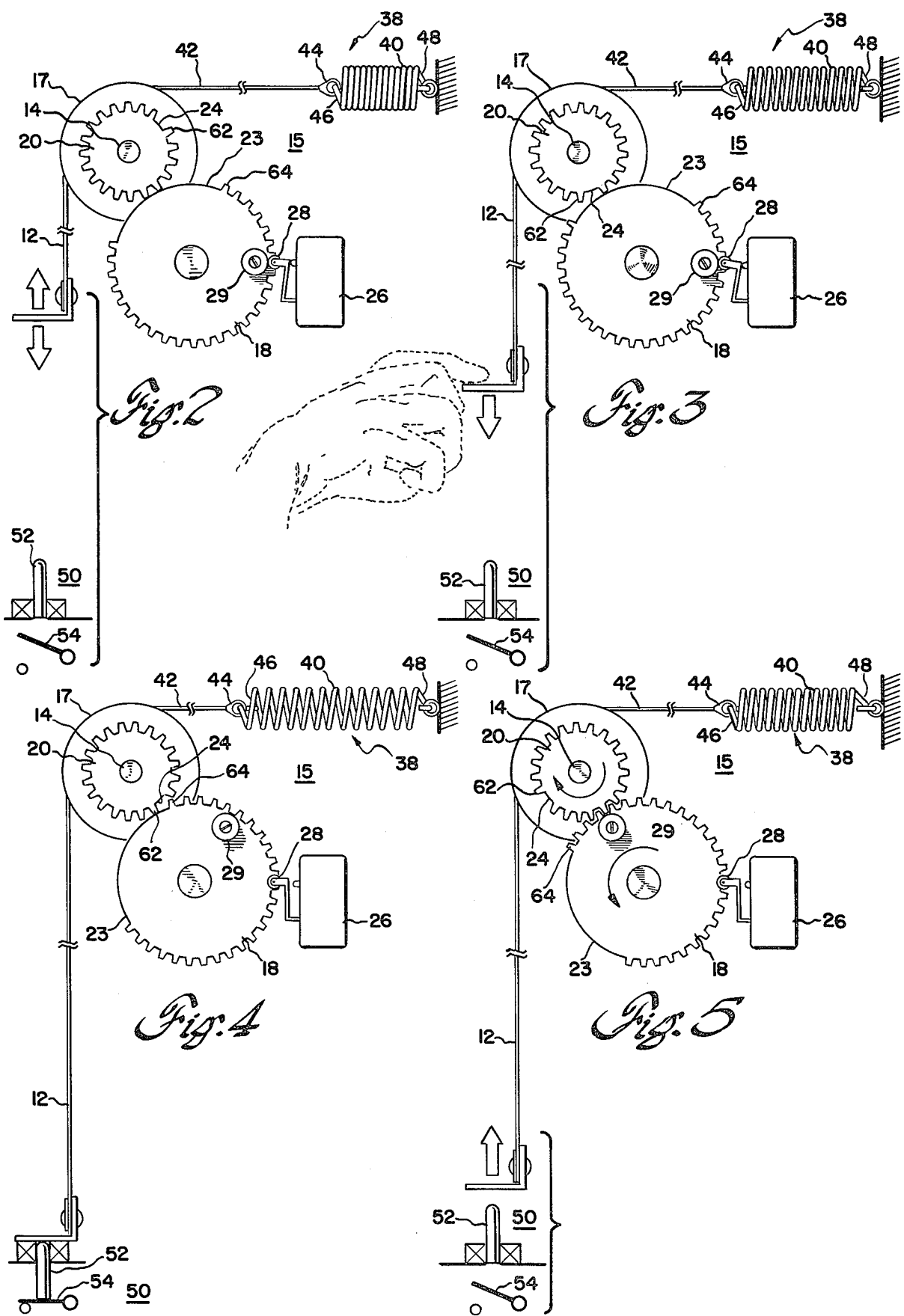

X-RAY APPARATUS AND CLOSURE MECHANISM THEREFOR

This is a continuation of U.S. application Ser. No. 864,504, filed Dec. 27, 1977, now abandoned, and the benefits of such earlier application are hereby claimed for the present application.

BACKGROUND OF THE INVENTION

The present invention is directed to a closure mechanism especially suited for X-ray inspection apparatus.

It has become necessary for safety and law enforcement purposes, to inspect various articles, such as suitcases, briefcases, packages, etc., that are brought into or taken out of a building or onto an airplane, put in the mail, etc., to detect weapons or other contraband and/or valuable items which may be stolen. As a result, it has been necessary to inspect large volumes of such articles, thereby requiring the inspection apparatus to be operable quickly and efficiently, including the time required to introduce an article into the apparatus and remove it after inspection. Such inspection apparatus are desired to have good reliability and low cost so as to propagate their use for achieving the ends of safety, law enforcement, and theft control.

One type of inspection apparatus is that which contains a compartment into which an article, such as a briefcase or package, is placed and inspected by means of X-rays. It is desirable that such apparatus have a short loading and inspection cycle time, to maximize their throughput, but such must not be at the risk of safety to persons using and present near the apparatus.

The present invention serves to achieve the goal of a relatively high volume inspection device, with satisfactory safety (i.e., X-radiation safety) features and relative ease of use.

SUMMARY OF THE INVENTION

An apparatus for inspecting various articles and comprising means for operating a retractable door, comprising a shaft member, a flexible door member carried by and windable on the shaft member, motor means for driving the shaft member, a gear train mechanically linking the motor means and the shaft member, the gear train comprising a drive gear and a driven gear, the driven gear being connected to the shaft member and the drive gear being connected to and driven by the motor, the drive and driven gears comprising gear teeth about only a portion of their respective circumferences, switch means for controlling the motor, and said drive gear comprising means for actuating the switch means.

BRIEF DESCRIPTION OF THE DRAWING

FIG. 1 is a isometric view of a portion of the mechanism of the apparatus according to a preferred embodiment of the invention.

FIGS. 2–5 depict schematically a part of the door-opening structure of the mechanism in FIG. 1.

FIG. 6 is a perspective view of the apparatus with which the mechanism can be employed.

PREFERRED EMBODIMENT

Figure 7:
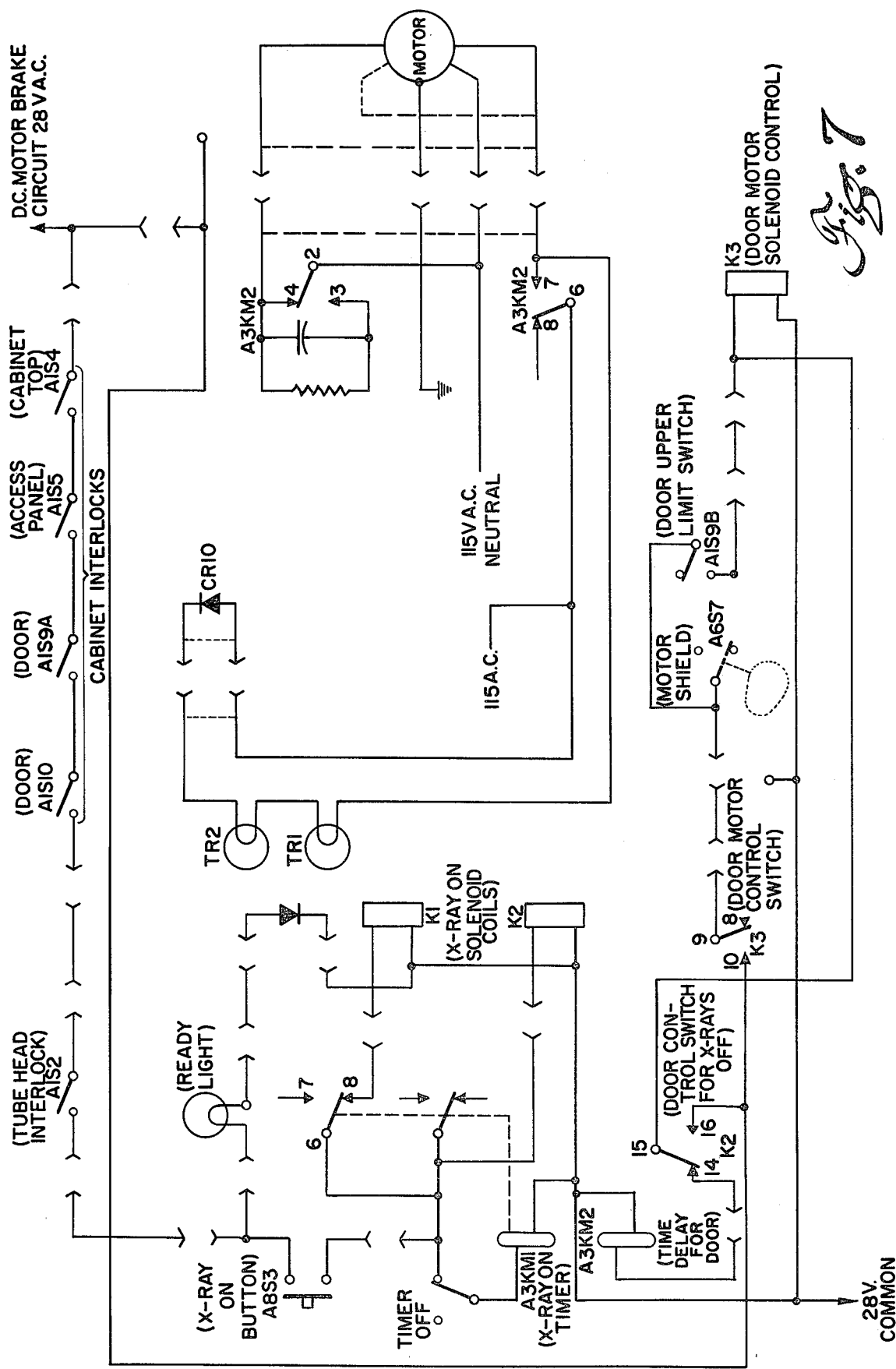
FIG. 7 is a schematic diagram, according to a preferred embodiment, of the circuitry for operating the present apparatus and mechanism.

Referring to the drawings, the apparatus 10 of the present invention comprises a mechanism 11 for operating a retractable door 12, the mechanism comprising a shaft or roller member 14 that carries and can take up or wind up the door member 12. The door member 12 preferably is flexible (as used herein, the term "flexible" is defined to include doors that are truly flexible, e.g., rubberized material, as described later herein, and doors that consist of inflexible sections that are hingedly connected to each other). Where it is desired, a drum 17 can be mounted on the shaft 14, the door 12 being wound onto and off of such drum 17.

The apparatus 10 further comprises a drive mechanism, e.g., a gear train 15 and a motor 16 for driving the shaft member 14 and, therefore, moving the door 12 between open and shut positions. The gear train 15 preferably comprises a drive gear 18 connected to the motor 16 and a driven gear 20, the driven gear being located on the shaft member 14 and engaging the drive gear 18, which is located on the rotor or shaft 22 of the motor 16. Both of the drive and driven gears 18, 20 comprise respective peripheral parts that do not have gear teeth, each of these gears 18 and 20, having, according to a more preferred embodiment, two teeth missing for the reasons given below.

The apparatus 10 preferably includes also a switch member or means 26 for controlling the motor. The motor switch 26 can include a trip element 28 and the drive gear 18 can include a lug 29 or other protrusion for engaging the trip element 28 and turning the motor 16 on and/or off, as explained below.

The apparatus 10 defines a chamber 30 that is partially defined by the door member 12, access to the chamber 30 being gained via the passageway provided by the opened door member 12. The chamber 30 should be X-ray tight, with the walls defining the chamber comprising X-ray impermeable material. Where it is desired, the switch 26 can be mounted on a wall 32 comprising a slot or opening 34 in which a part of the shaft or roller 14 is located, the apparatus preferably comprising bearings in which end portions (or parts near the ends) of the shaft 14 are journalled. Because the chamber must be X-ray tight, necessary safeguards should be taken to ensure against X-rays escaping into the vicinity of the apparatus via the slot 34.

The mechanism 11 preferably also comprises a pulley element 36 (FIG. 1) mounted on and fixed to the shaft 14 to rotate with the shaft 14. Biasing means 38 are included in the apparatus to counter-act the weight of the door member 12 when the latter is not in the open, or up, position, this to facilitate opening the door as explained below. In one form, the biasing means 38 can include a helical spring 40 and a filamentary member 42, such as flexible steel rope. One end of the filamentary member 42 is fixed to the pulley element 36 and the other end 44 is connected to the end 46 of the spring 40, which has its other end 48 secured or anchored to an immovable part, such as a wall of the structure. When the door 12 is down, the spring 40 is extended, as shown in FIG. 4, the spring 40 being adapted to exert by itself, a force less than that sufficient to lift the door 12 from the closed position, it being preferred however, that the spring force be only somewhat less than that needed to open the door by itself.

The above mechanism can be used in, inter alia, inspection apparatus utilizing X-rays, in which there is a structure or cabinet defining a chamber or compartment 30 which is substantially impermeable to X-rays and which is closed off by the door member 12, which, in this case, also is substantially impermeable to X-rays. In this case, the present apparatus further comprises an interlocking system by means of which X-rays are not produced in the apparatus unless the door member 12 is closed, so as to avoid accidental exposure of personnel or others to the X-rays. The interlocking system can comprise at least one further switch 50 (FIGS. 2-5) that includes a button portion 52 which normally is in a raised position (FIG. 2) (e.g., the button portion can include suitable biasing means that hold the button in the raised position) and a contact portion 54 that normally is in the open position. The button and contact portions 52, 54 are arranged below the door 12, so that when the latter is closed, it contacts and depresses the button 52, which, in turn, closes the contact 54. The contact 54 is in a circuit (described hereinafter) that controls the X-ray generating means (e.g., an X-ray tube 55 in FIG. 1) of the apparatus, so that when the button 52 is raised and the contact 54 is open, the circuit will be broken and no X-rays can be generated, whereas, when the button 52 is depressed by the lowered door 12, the contact 54 will be closed and the X-ray circuit can operate.

In the operation of the apparatus 10, which in this instance is an X-ray inspection apparatus for inspecting various articles, the door 12 is in the up or open position (FIG. 2), the article that is to be inspected being placed in the X-ray proof compartment or chamber 30 that is partially enclosed by the door 12. With the door 12 in this open position, the door is wound on the roller member 14 and the toothless peripheral portion 23 of the drive gear 18 is located at the driven gear 20 so that the gears do not mesh.

As the door is pulled down to close the compartment 30, the driven gear 20 turns in, e.g., the counter-clockwise direction, with the drive gear 18 remaining stationary, the biasing means or spring 40 becoming loaded, or extended, as the door is lowered (FIG. 3).

With the door 12 in its closed position (FIG. 4), the driven gear 20 is located such that the last gear tooth 62 thereof is located adjacent to the first gear tooth 64 of the drive gear 18 (which first and last gear teeth 64, 62 bound the toothless portions 23 and 24, respectively, of their respective gears 18 and 20), so that, upon the counter-clockwise rotation of the drive gear 18 by operating the motor 16, the first gear tooth 64 thereof will engage the last gear tooth 62 of the driven gear 20. The spring 40 is, under these circumstances, fully extended. At this stage of operation, the button portion 52 of the switch is depressed by the lower portion of the door member 12, the contact portion 54 being closed by the depressed button portion 52 and thus closing the interlock system to permit the energization of the X-ray producing device 55 of the apparatus 10. While the door 12 is in this lowered or closed position, the switch contact 54 remains closed and the X-rays can be produced, the lowered door member 12 closing the compartment 30 so that there is no X-radiation exposure of anyone present in the vicinity of the apparatus 10.

At a further stage of operation of the apparatus 10, when the desired inspection or other utilization of the apparatus 10 has been done, the door member 12 is raised by activating the drive motor 16 and, thus, driving the drive gear 18 such that the driven gear 20 rotates in the direction (i.e. clockwise) opposite its rotational direction when the door 12 was closed, i.e., the drive gear is rotated in the counter-clockwise direction. As a result, the drum or roller member 17 is rotated and winds up the door member 12. As the door member 12 is raised, the button portion 52 of the switch 50 is released and rises allowing the contact portion 54 to open and, thus, preventing the generation of X-rays while the door member 12 is open.

The rotation of the drive gear 18 by the drive motor 16 until the lug element 29 located on the drive gear 18 engages the trip element 28 of the motor switch 26 and causes the motor 16 to be turned off, at which point (FIG. 1) the door member 12 is raised fully and the toothless portion of the drive gear 18 is located adjacent the driven gear 20 such that the door member 12 can be subsequently lowered to a closed position without the driven gear 20 engaging the drive gear 18, as described above. Hence, the above described cycle can now be repeated.

A type of apparatus 70 with which the present mechanism can be employed is shown in FIG. 6, which depicts an X-ray inspection device for various articles. The apparatus comprises a source of X-rays (not shown) which are directed as a beam toward a chamber into which an article 72 has been placed via a door or entry port 74. The X-rays pass through the article 72 and form an image according to the article 72, the X-ray beam carrying such image then being converted to a visible image by means of a fluorescent screen and an optical system (not shown) which are contained in the X-ray impermeable cabinet 76 of the apparatus 70. The visible image can then be viewed on a mirror 78. This type of apparatus is described in the application for U.S. patent filed concurrently herewith by David J. Haas et al. titled "X-ray Optical System For Article Inspection, With Components Disposed On Parallel Axes" Ser. No. 864,503, filed Dec. 27, 1977, now U.S. Pat. No. 4,297,580.

Describing generally the electronic circuitry of the present apparatus, the system is energized by turning on the key switch which is not relevant to the circuits but only supplies power after the key switch is on, 28 volts is now available as shown in the upper right corner. The system is initialized by loading an object into the X-ray chamber and closing the roll-up chamber door. When the door is closed, 28 volts of electricity now flows through the series of interlock switches at the upper part of the schematic: the access panels (A1S4), top cover (A1S5), two switches on the door of (A1S10, A1S9A) the interlock switches the two pairs then applies voltage, the interlock system is closed and voltage then flows to the ready light.

The ready light is DS5 which is on the front face of the machine so that the operator can see that the door is fully closed. In addition to turning on the ready light when the last microswitches are closed, voltages are applied to the X-ray on push-button momentary hand-switch A8S3. Upon pushing the handswitch machine is now ready to operate in an X-ray safe mode. Voltage is applied to relays K1 and K2 which turn on the X-rays by energizing the X-ray generator. In addition, voltages are applied to the A3KMI X-ray on timing circuit so that X-rays can only remain on a certain amount of time.

When K2 is turned on the X-rays go on, K2 contact 15 switches from contact 14 to 16 which now applies 28 volts to relay K3. K3 is the door enable relay. K3 upon energizing, self latches and remains on indicating that the X-rays have been on and that the door is now able to open when the X-ray button is turned off. K3 latches on by contacts 8 and 9, contact 9 is connected to contact 10 on K3 which latches the voltage on through the cam switch on the motor A6S7. The X-rays remain on until the operator lets his finger off the push button. The first thing that happens is that K1 and K2 de-energize and this then switches contact 15 on K2 to contact 14, which applies voltage to time delay relay A3KM2. This door delay relay is a half a second delay which prevents the door from rising for a half a second. The purpose of this is to permit the capacitors and the X-ray generators to discharge which is not relevant to the operation, it also permits the operator to push the button again if he decides that he wants to look at it further, so instead of having the door go up immediately when he lets his finger off the button, if he decides he wants a second view, he has a half a second to press the button again and the door will remain down. After the half a second time has timed out by A3KM2, this door relay closes contacts on the motor itself to start the motor driving. Contact 2 which is the common contact on A3KM2 moves to position 3 as well as contact 6 goes the position 7. This supplies 110 volts to the motor A6M1 and the motor starts driving the door up. Once the door has moved up, its top position is sensed by a switch on the cam on the motor which is switch A6S7 which sense the top position of the door, so the door does not over drive. As soon as the cam of the motor opens the contact on A6S7, the relay K3 de-energizes.

Once the door has gone up to the top, the microswitch has been actuated on the motor stop by the cam on the motor, it removes the voltage from the relay K3, K3 de-energizes and when K3 de-energizes its contact from 9 to 10 open and puts the contact from 9 to 8 and this in turn removes the voltage from KM2 which lets the door relay A3KM2 to remove 110 volts from the motor and the motor stops. Then the cycle can be repeated by simply closing the door again which is manually pulled down. Switch A1S9D is simply a by-pass switch in case the motor stops so that the motor stop switch is open, A1S9D is the switch in the bottom of the door so that when the door is closed S9D is closed to be sure that power can be applied to KM2 so that this motor will start driving up. It can happen that the motor will stop with the cam leaving A6S7 open and therefore power will not be available to latch on K3 to hold the power on the motor.

When the door relay switch A3KM2 de-energizes, the contacts now switch across from A3KM2 from 2 to 3, the contact goes from 2 to 4, and this shorts out the capacitor so that the braking circuit which goes through the motor at all times doesn't have to buck the capacitor. The braking circuit is a series of two light bulbs which are TR1 and TR2. A direct current diode CR10 is in series so that when the motor de-energizes, the motor then receives a surge of DC current through the cold light bulbs (and therefore low resistant) into the motor. It receives a substantial amperage DC current which makes an electrical brake in the motor. The motor then stops instantly and after about 15 milliseconds the light bulbs warm up and reduce the current through the motors so that the motor does not overheat thus, the purpose of the light bulbs and the diode is to make a direct current braking through the motor for a very short period of time and then reduce the current so that the motor will remain fixed in that position, keeping the microswitch cam and A6S7 in exactly the right position. This latter light bulb circuit could be replaced by a somewhat more complicated relay circuit. However, its purpose is to electrically stop the motor in exactly the right position with the roll-up door at the correct top position.

We claim:

1. An apparatus for inspecting various articles comprising
    a chamber defining structure including enclosing walls and a retractable door, said structure being substantially impermeable to X-rays,
    a shaft member inside said structure and provided for carrying said retractable door, said retractable door including a flexible construction windable on said shaft member, wherein winding said flexible construction onto said shaft member opens said chamber and unwinding said flexible construction from said shaft member closes said chamber,
    motor means for driving said shaft member in rotation,
    a gear train mechanically linking said motor means and said shaft member, said gear train including a drive gear driven by said motor means and having gear teeth only about a portion of its circumference, and a driven gear connected to said shaft member and having gear teeth only about a portion of its circumference,
    said driven gear being moved independently of said drive gear upon closing said chamber, and said drive gear engaging said driven gear upon opening said chamber, and
    switch means actuated by said drive gear for controlling said motor means.

2. An apparatus according to claim 1, wherein said structure further includes X-ray means in said chamber for directing X-rays to a predetermined part of said chamber, and control means for controlling said X-ray means, said control means also controlling said motor means independently of said switch means.

3. An apparatus according to claim 2, wherein said chamber structure receives an article to inspection through said retractable door, said article being provided in said chamber structure at an area where said X-rays are directed, and wherein said chamber structure further includes means receiving X-rays transmitted through said article for converting transmitted radiation into a visual image.

4. An apparatus according to claim 2, wherein said control means are provided by electrical circuit means for operating said X-ray means, said circuit means including a safety switch being in an open condition when said retractable door is open and being in a closed condition when said retractable door is closed such that X-rays are provided only when said retractable door is closed.

5. An apparatus according to claim 4, wherein said switch means actuated by said drive gear also controls generation of X-rays, said switch means starting said motor means to drive said drive gear when said X-ray means is turned off such that said retractable door is opened by rotation of said shaft member.

6. An apparatus according to one of claims 1, 2, or 5, wherein a pulley member is disposed on said shaft member, and biasing means are connected to said pulley member for exerting a force on said pulley member when said retractable door is closed only somewhat less than that needed to open said retractable door.

7. An apparatus according to claim 6, wherein each of said drive gear and said driven gear have two gear teeth missing.

8. An apparatus according to claim 6, wherein said biasing means substantially counter-balances said retractable door.

9. An apparatus according to claim 6, wherein said biasing means includes a spring member being in an expanded condition when said retractable door is closed.

10. An apparatus according to claim 6, wherein said biasing means includes a biasing element secured at one end to an anchoring element attached to an interior wall of said structure, and a flexible line member attached to a second end of said biasing element and passing to said pulley member, said flexible line member being wound on said pulley member when said retractable door is open.

11. An apparatus according to claim 6, wherein a lug element is provided on said drive gear for actuating said switch means.

12. An apparatus according to claim 11, wherein said switch means includes a microswitch element.

13. An apparatus according to claim 6, wherein said shaft member is journaled in bearings at opposite ends thereof.

14. An apparatus according to claim 1, wherein said retractable door is completely opened in a single revolution of said drive gear.

* * * * *

UNITED STATES PATENT AND TRADEMARK OFFICE
CERTIFICATE OF CORRECTION

PATENT NO. : 4,379,481
DATED : April 12, 1983
INVENTOR(S) : ADOLPH JUNER ET AL

It is certified that error appears in the above—identified patent and that said Letters Patent is hereby corrected as shown below:

Claim 3, Line 2, change "to" to --for--.

Signed and Sealed this

Twenty-first Day of June 1983

[SEAL]

Attest:

DONALD J. QUIGG

*Attesting Officer*   *Acting Commissioner of Patents and Trademarks*